(12) United States Patent
Turner

(10) Patent No.: US 10,654,632 B2
(45) Date of Patent: May 19, 2020

(54) FLEXIBLE CONTAINERS AND RELATED METHODS

(71) Applicant: B. Braun Medical Inc., Bethlehem, PA (US)

(72) Inventor: Robert E. Turner, San Clemente, CA (US)

(73) Assignee: B. Braun Medical Inc., Bethlehem, PA (US)

( * ) Notice: Subject to any disclaimer, the term of this patent is extended or adjusted under 35 U.S.C. 154(b) by 0 days.

(21) Appl. No.: 15/913,592

(22) Filed: Mar. 6, 2018

(65) Prior Publication Data
US 2018/0257835 A1 Sep. 13, 2018

Related U.S. Application Data

(60) Provisional application No. 62/468,801, filed on Mar. 8, 2017.

(51) Int. Cl.
*B65D 75/26* (2006.01)
*A61J 1/14* (2006.01)
(Continued)

(52) U.S. Cl.
CPC ............... *B65D 75/26* (2013.01); *A61J 1/10* (2013.01); *A61J 1/1468* (2015.05); *A61J 1/1475* (2013.01);
(Continued)

(58) Field of Classification Search
CPC .. B65D 75/26; B65D 75/525; B65D 75/5855; B65D 75/5861; B65D 75/5883;
(Continued)

(56) References Cited

U.S. PATENT DOCUMENTS 3,982,992 A * 9/1976 Moffitt .................... B29C 65/18
156/583.4
4,064,302 A 12/1977 Koslowski et al.
(Continued)

FOREIGN PATENT DOCUMENTS

CH 701906 A1 3/2011
EP 1462078 A1 9/2004
(Continued)

OTHER PUBLICATIONS

Machine translation of JP-06039018-A.*
(Continued)

*Primary Examiner* — Jes F Pascua
(74) *Attorney, Agent, or Firm* — Klein, O'Neill & Singh, LLP

(57) ABSTRACT

A flexible container incorporating flexible front and rear sheets with a perimeter seal in which at least one length or section of the perimeter seal can include a seal weld that has both a permanent seal section and a pressure absorbing seal section. The pressure absorbing seal section is configured to peel, fail, or split when the flexible container, filled with a solution or liquid, is dropped onto a hard surface to thereby absorb the impact of the drop. The flexible container can be provided with one or more dispensing and/or additive ports or without any port. The flexible container may include more than one compartments with a peelable seal separating two adjoining compartments of the flexible container.

23 Claims, 5 Drawing Sheets

(51) Int. Cl.

| | | |
|---|---|---|
| *A61J 1/20* | (2006.01) | |
| *A61M 3/02* | (2006.01) | |
| *B65D 75/58* | (2006.01) | |
| *B65D 75/52* | (2006.01) | |
| *B29C 65/20* | (2006.01) | |
| *B29C 65/24* | (2006.01) | |
| *B29C 65/00* | (2006.01) | |
| *A61J 1/10* | (2006.01) | |
| *B29C 65/18* | (2006.01) | |
| *B29C 65/82* | (2006.01) | |
| *B65D 81/32* | (2006.01) | |
| *B29C 65/76* | (2006.01) | |
| *B29K 623/00* | (2006.01) | |
| *B29L 31/00* | (2006.01) | |
| *B29K 705/02* | (2006.01) | |

(52) U.S. Cl.
CPC .......... *A61J 1/2024* (2015.05); *A61J 1/2093* (2013.01); *A61M 3/0279* (2013.01); *B29C 65/18* (2013.01); *B29C 65/20* (2013.01); *B29C 65/24* (2013.01); *B29C 65/76* (2013.01); *B29C 65/8223* (2013.01); *B29C 66/1122* (2013.01); *B29C 66/232* (2013.01); *B29C 66/242* (2013.01); *B29C 66/244* (2013.01); *B29C 66/346* (2013.01); *B29C 66/3452* (2013.01); *B29C 66/43* (2013.01); *B29C 66/4326* (2013.01); *B29C 66/71* (2013.01); *B29C 66/73921* (2013.01); *B29C 66/81419* (2013.01); *B29C 66/81425* (2013.01); *B29C 66/81427* (2013.01); *B29C 66/81433* (2013.01); *B29C 66/8322* (2013.01); *B29C 66/83221* (2013.01); *B29C 66/8511* (2013.01); *B29C 66/92451* (2013.01); *B65D 75/525* (2013.01); *B65D 75/5855* (2013.01); *B65D 75/5861* (2013.01); *B65D 75/5883* (2013.01); *B65D 81/3266* (2013.01); *A61J 1/1462* (2013.01); *B29C 66/342* (2013.01); *B29C 66/53262* (2013.01); *B29C 66/7234* (2013.01); *B29C 66/72321* (2013.01); *B29C 66/849* (2013.01); *B29C 66/919* (2013.01); *B29C 66/949* (2013.01); *B29C 2795/00* (2013.01); *B29K 2623/12* (2013.01); *B29K 2705/02* (2013.01); *B29L 2031/712* (2013.01); *B29L 2031/7128* (2013.01); *B29L 2031/7148* (2013.01)

(58) Field of Classification Search
CPC ... B65D 81/3266; A61J 1/1468; A61J 1/2024; A61J 1/10; A61J 1/1475; A61J 1/2093
USPC .......................................... 383/107, 108, 38
See application file for complete search history.

(56) References Cited

U.S. PATENT DOCUMENTS

| | | |
|---|---|---|
| 4,183,434 A | 1/1980 | Watt |
| 4,576,285 A | 3/1986 | Goglio |
| 4,667,453 A | 5/1987 | Goglio |
| 4,705,174 A | 11/1987 | Goglio |
| 4,711,359 A | 12/1987 | White et al. |
| 4,759,472 A | 7/1988 | Strenger |
| 4,770,295 A | 9/1988 | Carveth et al. |
| 5,176,634 A * | 1/1993 | Smith .................. A61J 1/2093 206/219 |
| 5,910,138 A | 6/1999 | Sperko et al. |
| 5,928,213 A | 7/1999 | Barney et al. |
| 5,944,709 A | 8/1999 | Barney et al. |
| 6,007,529 A | 12/1999 | Gustafsson et al. |
| 6,117,123 A | 9/2000 | Barney et al. |
| 6,149,304 A | 11/2000 | Hamilton et al. |
| 6,165,161 A | 12/2000 | York et al. |
| 6,203,535 B1 | 3/2001 | Barney et al. |
| 6,361,642 B1 | 3/2002 | Bellamy et al. |
| 6,398,771 B1 | 6/2002 | Gustafsson et al. |
| 6,468,377 B1 | 10/2002 | Sperko et al. |
| 6,764,567 B2 | 7/2004 | Sperko et al. |
| 6,823,994 B2 | 11/2004 | Tsaur |
| 6,846,305 B2 | 1/2005 | Smith et al. |
| 6,913,388 B2 | 7/2005 | Laske |
| 6,952,959 B2 | 10/2005 | Hishinuma |
| 6,996,951 B2 | 2/2006 | Smith et al. |
| 7,055,683 B2 | 6/2006 | Bourque et al. |
| 7,306,371 B2 | 12/2007 | Perell |
| 7,527,619 B2 | 5/2009 | Domkowski et al. |
| 7,546,918 B2 | 6/2009 | Gollier et al. |
| 7,618,405 B2 | 11/2009 | Young |
| 7,862,869 B2 | 1/2011 | Papenfuss et al. |
| 7,875,015 B2 | 1/2011 | Pahlberg et al. |
| 7,875,016 B2 | 1/2011 | Pahlberg et al. |
| 7,900,471 B2 | 3/2011 | Leske |
| 8,025,169 B2 | 9/2011 | Zimmerman |
| 8,028,850 B2 | 10/2011 | Zimmerman |
| 8,100,276 B2 | 1/2012 | Moor |
| 8,449,520 B2 | 5/2013 | Pepper et al. |
| 8,590,282 B2 | 11/2013 | Perell et al. |
| 8,777,922 B2 | 7/2014 | Inoue et al. |
| 8,794,487 B2 | 8/2014 | Maas et al. |
| 9,205,952 B2 | 12/2015 | Maas et al. |
| 9,237,985 B2 | 1/2016 | Eckhoff et al. |
| 9,278,051 B2 | 3/2016 | Inoue et al. |
| 9,365,339 B2 | 6/2016 | Perell et al. |
| 9,469,088 B2 | 10/2016 | Stanley et al. |
| 9,662,869 B2 | 5/2017 | Julien |
| 9,682,526 B2 | 6/2017 | Julien |
| 9,684,601 B2 | 6/2017 | Bottcher et al. |
| 9,802,745 B2 | 10/2017 | Perell et al. |
| 2004/0223801 A1 | 11/2004 | Detwiler et al. |
| 2008/0095476 A1* | 4/2008 | Holzwarth .............. B29C 65/76 383/107 |
| 2010/0133278 A1* | 6/2010 | Peluso ................... B32B 27/32 220/500 |
| 2014/0033653 A1 | 2/2014 | Cham et al. |

FOREIGN PATENT DOCUMENTS

| | | | | |
|---|---|---|---|---|
| JP | 55154118 A | * | 12/1980 | ......... B29C 66/1122 |
| JP | 06039018 A | * | 2/1994 | |
| JP | 2004000476 A | * | 1/2004 | ............. B29C 66/21 |
| JP | 2007007128 A | * | 1/2007 | ......... B29C 66/1122 |
| JP | 2007075276 A | * | 3/2007 | ........... B29C 66/723 |
| JP | 2016202467 A | * | 12/2016 | ................ A61J 1/10 |
| WO | WO 03/066471 A1 | | 8/2003 | |
| WO | WO 2015/056605 A1 | | 4/2015 | |

OTHER PUBLICATIONS

Machine translation of JP-55154118-A.*
Invitation to Pay Additional Fees and, Where Applicable, Protest Fee with Partial International Search on corresponding PCT application (PCT/US2018/021343) from International Searching Authority (EPO) dated Jun. 1, 2018.
International Search Report and Written Opinion on corresponding PCT application (PCT/US2018/021343) from International Searching Authority (EPO) dated Aug. 2, 2018.
International Preliminary Report on Patentability (Chapter I) on corresponding PCT application (PCT/US2018/021343) from International Searching Authority (EPO) dated Sep. 19, 2019.

* cited by examiner

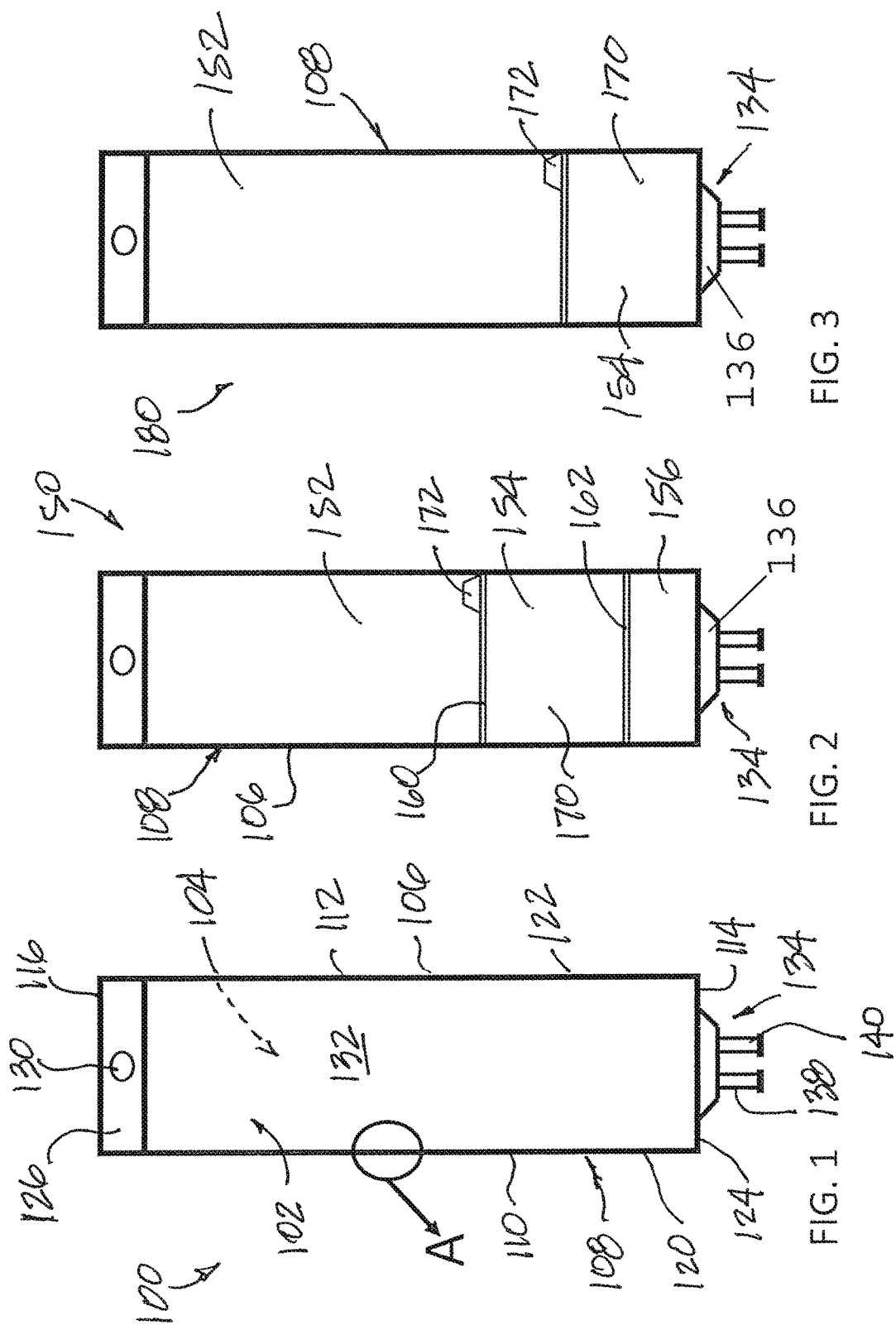

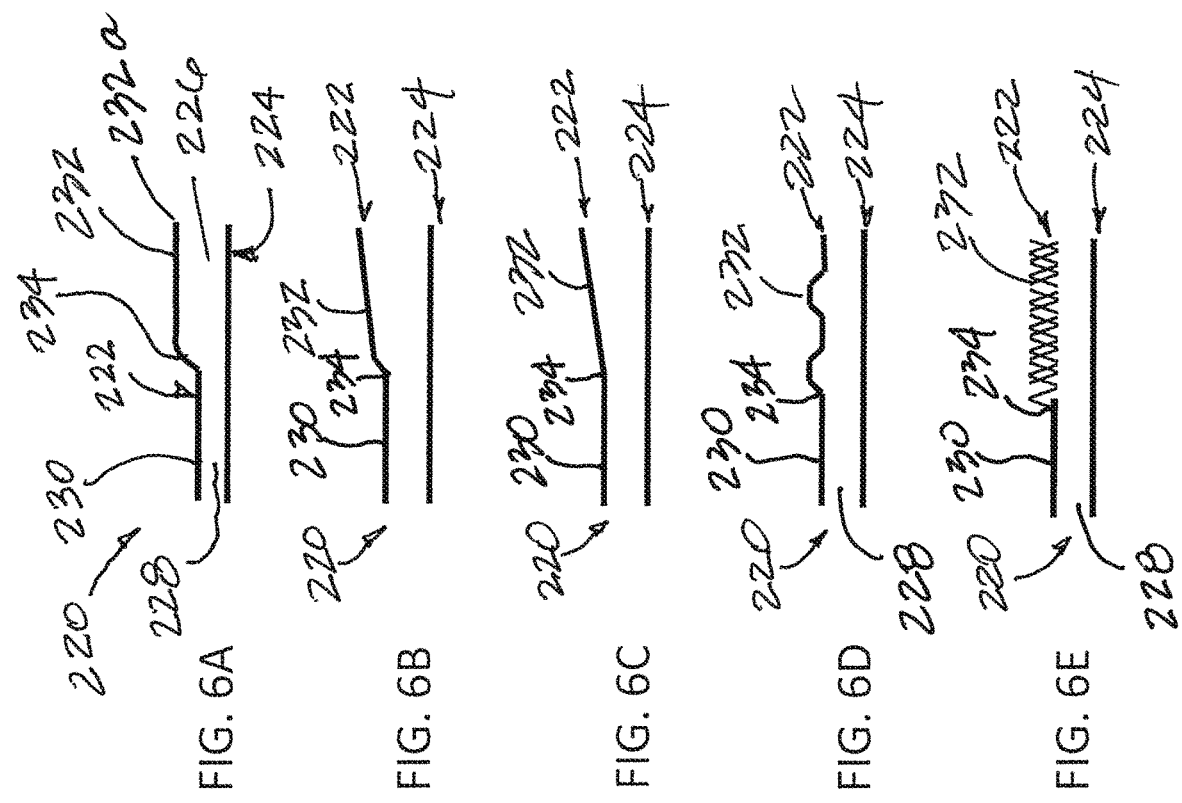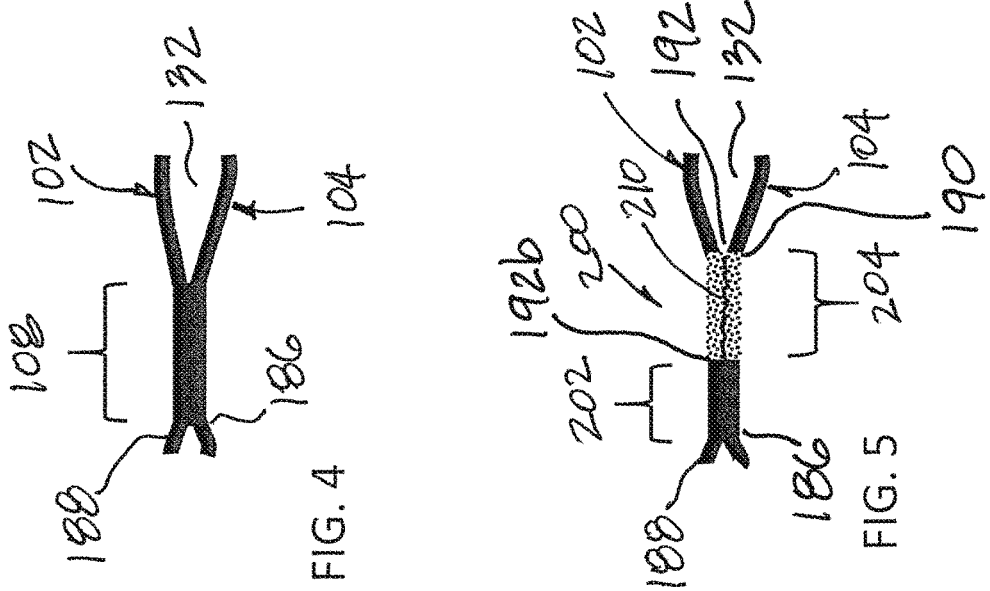

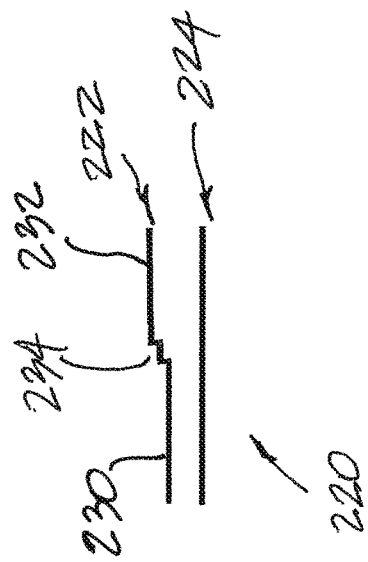
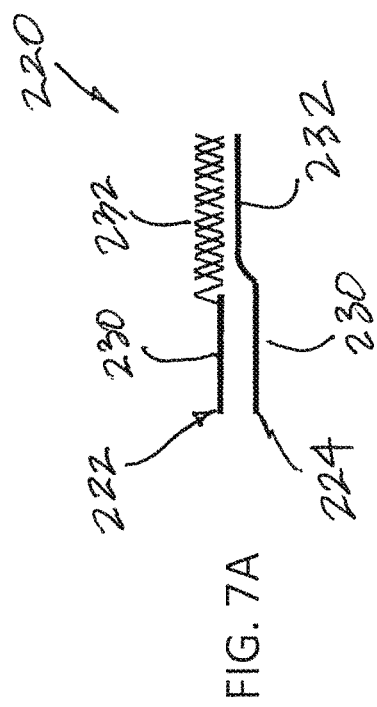
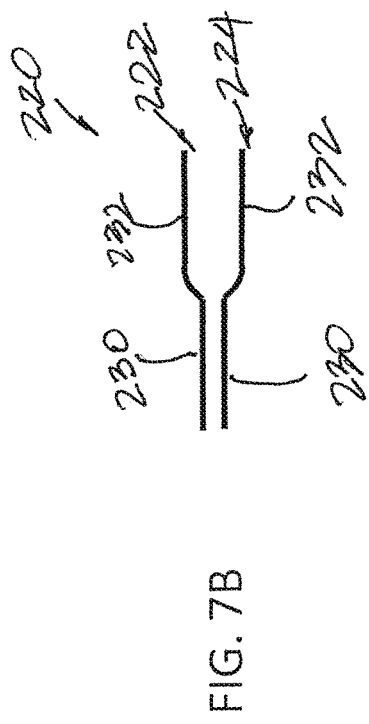

FLEXIBLE CONTAINERS AND RELATED METHODS

FIELD OF ART

Flexible containers having a flexible front sheet sealed along a perimeter to a flexible rear sheet are generally discussed herein with particular discussions on flexible containers having perimeter seals with rupture absorbing seal components and related methods.

BACKGROUND

Flexible containers are widely used for packaging nutritional fluids, diluents, medicaments, IV solutions, dietary supplements, cooking ingredients, and the like. Broadly speaking, these flexible containers are manufactured by affixing a first flexible sheet to a second flexible sheet along a perimeter and interposing one or more ports in between the two sheets for filling, for draining, and/or for supplementing or adding other fluids to the container. Some flexible containers are commercialized without any dispensing nozzle or port but with one or more weakened sections to facilitate access. The sheets used to make the flexible containers may be made from single-layer flexible thermoplastic sheets or from multiple-layers flexible thermoplastic sheets. A single port is typically incorporated with the container for dispensing only but can also include a fluid additive port for adding fluids, supplements or products into the container. The flexible container may include peelable seals that extend between side edges of the container to form compartments within the container for separately storing two or more different solutions or products.

SUMMARY

A flexible container is described. The flexible container can comprise a first sheet attached to a second sheet along a perimeter with a perimeter seal, said perimeter comprising first and second long edges and first and second short edges, and said first and second sheets each comprising an exterior surface and an interior surface; wherein the perimeter seal has a permanent seal section and a pressure absorbing seal section along a cross-section and along at least one section of the first and second long edges and the first and second short edges, and wherein the pressure absorbing seal section of the perimeter seal has a separation characteristic value that is lower than the separation characteristic value of the permanent seal section.

The flexible container can further comprise at least one peelable seal attaching the interior surfaces of the first and second sheets together and the at least one peelable seal extending between the two long edges.

The permanent seal section and the pressure absorbing seal section can extend an entire length of at least one of the first long edge, the second long edge, the first short edge, and the second short edge.

The flexible container can include a fluid dispensing system attached at the first short edge.

A further aspect of the present disclosure includes a heat die assembly for forming a perimeter seal of a flexible container. The heat die assembly can comprise a first heat die spaced from a second heat die, said first heat die comprises a permanent seal welding section and an absorbing seal welding section, wherein when the second heat die is placed subjacent the first heat die or when the first heat die is placed superjacent the second heat die, a variable gap is defined by the first and second heat dies; and wherein a gap between the permanent seal welding section of the first heat die and the second heat die is smaller than a gap between the absorbing seal welding section and the second heat die.

The first heat die and the second heat die can have the same shape or different shapes.

A still further aspect of the present invention includes a flexible container comprising: a first sheet attached to a second sheet along a perimeter with a perimeter seal, said perimeter comprising first and second long edges and first and second short edges, and said first and second sheets each comprising an exterior surface and an interior surface; wherein the perimeter seal has a permanent seal section and a pressure absorbing seal section along a cross-section and along at least one section of the first and second long edges and the first and second short edges, and wherein the pressure absorbing seal section of the perimeter seal has a separation characteristic value that is lower than the separation characteristic value of the permanent seal section.

The flexible container can include at least one peelable seal attaching the interior surfaces of the first and second sheets together and the at least one peelable seal can extend between the two long edges.

The permanent seal section and the pressure absorbing seal section of the perimeter seal described herein can extend an entire length of at least one of the first long edge, the second long edge, the first short edge, and the second short edge or all of the edges.

The flexible container can further comprise a fluid dispensing system attached at the first short edge.

The fluid dispensing system can comprise at least one nozzle. In some examples, there can be two nozzles. The nozzles can include a terminal end for use with an IV spike or a male Luer.

The first sheet, the second sheet or both the first sheet and the second sheet can be made from a polypropylene (PP) based material.

The permanent seal section can have a width and the pressure absorbing seal section can have a width, and wherein the width of the permanent seal section is at least two times greater than the width of the pressure absorbing seal section.

The width of the pressure absorbing seal section can have a larger value than a radiused corner.

An opaque protective cover can be located over the exterior surface of the front sheet, the rear sheet, or on both flexible rear sheet and front sheet.

The front sheet or rear sheet or both can be a multi-laminate sheet having multiple layers. The multiple layers can include an aluminum foil layer.

A still further aspect of the present invention is a heat die assembly comprising: a first heat die spaced from a second heat die, said first heat die comprising a perimeter weld element comprising a weld surface with a permanent seal welding section and a pressure absorbing seal welding section and said second heat die comprising a perimeter weld element having a weld surface; wherein when the second heat die is placed subjacent the first heat die or when the first heat die is placed superjacent the second heat die, a variable gap is defined by the first and second heat dies; and wherein a gap between the permanent seal welding section of the first heat die and the weld surface of the second heat die is smaller than a gap between the pressure absorbing seal welding section and the weld surface of the second heat die.

The perimeter weld element of the heat die can have two spaced apart side weld elements.

A plurality of spaced apart purging orifices can be located inside a boundary defined by a perimeter weld element.

The permanent seal welding section and the pressure absorbing seal welding section described herein can be provided along an entire length of the two spaced apart side weld elements.

An end weld element can connect to the two spaced apart side weld elements.

The heat die assembly can comprise two spaced apart perimeter rails.

Each perimeter rail can comprise an alignment boss.

A still yet further aspect of the present invention includes a method of manufacturing a flexible container. The method can comprise: placing a flexible front sheet and a flexible rear sheet in between two heat dies; apply heat to the two heat dies to join the flexible front and rear sheets along a perimeter seal; wherein the perimeter seal has a permanent seal section and a pressure absorbing seal section along a cross-section and wherein the pressure absorbing seal section of the perimeter seal has a separation characteristic value that is lower than the separation characteristic value of the permanent seal section.

The method can further comprise placing a dispensing port system between the flexible front sheet and the flexible rear sheet prior to placing the flexible front and rear sheets between the two heat dies.

The method can further comprise placing alignment pins in through alignment bosses formed with the two heat dies.

A flexible container provided in accordance with aspects of the present devices, systems, and methods can be sized and shaped to accommodate a wide range of available volumetric requirements. The flexible container may be formed by attaching a flexible front or first sheet to a flexible rear or second sheet and sealing the perimeter of the two sheets with a perimeter seal.

A container perimeter provided herein is understood to include a first side edge, a second side edge, a bottom or lower edge, and a top or upper edge, elevation-wise.

The perimeter seal can be formed as a permanent seal in that the seal is not intended to be separable or peelable without tearing the front and/or rear sheets or without allowing or permit liquid contained within the flexible container to leak through the perimeter seal. The perimeter seal along the edges of the container therefore include a first side permanent seal, a second side permanent seal, a bottom or lower permanent seal, and a top or upper permanent seal.

In some examples, the upper permanent edge seal can be wider than the lower permanent edge seal and/or the two side permanent seals. The wider upper permanent edge seal can provide room or space to incorporate a perimeter defining a hole for use with a hook to hang the flexible container, such as for dispensing or for displaying.

Optionally, a dispensing port system can be provided with the bottom permanent seal, such as placed between the front and rear sheets and then heat sealed to the front and rear sheets to dispense fluid or contents from the enclosed space within the container along the bottom edge. The dispensing port system can have a saddle, a first port or nozzle and second port or nozzle. Terminal ends can be provided with each nozzle. The terminal ends can be sized and shaped to receive an IV spike, can include a septum for puncture by a needle, or can include a movable piston or a needleless connector for receiving a Luer tip. Optionally, only one port is included.

Still further, the port system may be omitted altogether and the flexible container is provided with a weakened section, such as a puncture site, for puncturing using a straw or the like to facilitate dispensing the contents from the enclosed space.

Terminal ends may be welded to the first and second ports for use with administrative tubing sets, such as an IV spike or drip line. The terminal ends, when used, may include a septum or a piston forming a needleless connector. The two ports may be provided with end fittings or caps for use as a fill port, a drain port, or an additive port.

In an example, the flexible container may be made from the same materials using the same methods as disclosed in U.S. Pat. No. 4,803,102 to Raniere et al., the contents of which are expressly incorporated herein by reference.

The front and rear sheets of the flexible container can each be a monolayer film or single ply film, can each be a multi-laminate film having multiple layers, or can be one of each, a monolayer film and a multi-laminate film. The two sheets can also be formed by taking a single elongated sheet and folding the single sheet to form two overlapping layers having a fold line and then sealing the open sides to form an enclosed space. One of the layers of the multi-layer film can comprise an opaque metal foil layer.

Any number of conventional monolayer films and multi-laminate films may be used to practice the container with perimeter seals with rupture absorbing seal components of the present disclosure. In an example, the films used to make the flexible container of the present disclosure can be one of various films disclosed in U.S. Pat. Nos. 4,803,102; 5,910,138; 5,928,213; 5,944,709; 6,165,161 and 6,203,535, the contents of each of which are expressly incorporated herein by reference.

In an example, the monolayer film material can be a polypropylene-based material, which can be the same PP-based material as the material used in commercially available EXCEL® IV bags. It is typical to mix or compound elastomeric materials in the base polypropylene material to obtain more flexible properties. The front and rear films of the flexible container can be the same or can be different.

When using a multilayer film, the multilayer film can be a polypropylene (PP)-based material. Each layer of the multi-layer film can have different properties or values, such as an outer layer that has a higher melting point to facilitate printing thereon and is less prone to sticking to heated tooling, an inner layer that bonds well to the mating film and ports yet has properties that allow for peelable-seals, and an inner layer that facilitates the barrier properties to prevent moisture loss.

The front and rear films or layers of the flexible container can be the same or can be different. One of the layers of the multi-layer film can include an opaque layer, such as an aluminum layer, to minimize UV light penetrating the contents of the flexible container. In a particular example, a PP-based multilayer film is used to form a flexible container or bag. The PP-based film may be the same as the film used in commercially available EXCEL® IV containers. The flexible container can have one of the following standard sizes: 250 mL, 500 mL, and 1000 mL. In other examples, the flexible container can have other sizes.

A flexible container provided herein can include multiple compartments, such as including an upper or first compartment, an intermediate or second compartment, and an outlet or third compartment.

A dispensing port system can be in fluid communication with the outlet compartment. The upper compartment and the intermediate compartment can be separated from one another by a first peelable seal that is designed to rupture or separate and the intermediate compartment can be separated from the outlet compartment by a second peelable seal, which can be designed to peel or separate upon application of pressure.

An optional opaque protective cover with a pull tab can extend or hang from the cover can be applied to the outer surface of the intermediate compartment to provide extra protection, such as from light or moisture, for the contents inside the intermediate compartment, which can contain a medicament.

The first compartment can contain a liquid diluent. The outlet or third compartment can be an empty compartment to enable further mixing of the first two compartments prior to dispensing the mixed solution out the dispensing port system.

Prior to using the flexible container, the opaque protective cover can be removed, or partially lifted, by pulling on the pull tab to allow observation of the contents within the intermediate compartment, which can be a liquid or powder medicament.

A flexible container provided herein can have two compartments instead of three compartments. Thus, the compartment further away from the dispensing system can be called a first compartment and the compartment closer to the dispensing system can be called a second compartment. For example and compared to a flexible container with three compartments, the empty outlet compartment can be omitted. Further, while a protective cover is preferred when certain drugs or medicaments are incorporated inside a container, such additional protective cover can be omitted.

In some examples, flexible containers are provided without any dispensing port or provided with a dispensing port system having just one port or more than two ports. The various flexible containers disclosed herein may be used for any number of applications, including for drinks, dietary applications, irrigation applications, and nutritional applications, among others.

A cross-sectional end view near a perimeter seal of the present disclosure typically shows a front sheet and a rear sheet joined to one another by the perimeter seal, which can be a first edge seal of a flexible container. The perimeter seal can also be used for the second edge seal opposite the first edge seal of the flexible container. The perimeter seal may also be used for the upper perimeter seal, the bottom perimeter seal or for all the perimeter seals of the flexible container. The perimeter seal at the different edges of the flexible container is preferably connected, such as formed using the same heat die assembly. A gap may be provided through one of the edges for filling the flexible container and/or to add a dispensing system.

An enclosed space is defined by the front and rear sheets of the flexible container. Along an outer edge of the perimeter seal opposite the enclosed space, there can be an overhang, which shows remnants of the front and rear sheets that have not been trimmed or have not been sealed-in to form part of the perimeter seal. Optionally, the overhang can be eliminated by trimming using any commercially available trimming means and the perimeter seal terminates at the outer edge, without the overhang.

The perimeter seal may be formed by applying the front and rear sheets between two heat dies and then pressing the heat dies together under a predetermined pressure, for a predetermined time, and heating the heat dies to a predetermined temperature to melt the inner most layers to then fuse the inner surfaces of the two layers together to form a seal, such as to form a perimeter seal of the present invention.

The time, temperature, and pressure utilized in the welding step can depend on the materials used for the front and rear sheets, the thickness of the front and rear sheets, the type of layers if a multi-layer film, and the thickness of the inner most layers that contact one another. For a polypropylene-based material, seal parameters of approximately 260° F.-310° F. and for about 0.5 sec to 2.0 sec can be used with heat dies to form the perimeter seals.

The weld pressure applied by the heat dies on the front and rear sheets can be the equivalent of compressing the two films approximately 15% to about 45% of the combined film thickness. Said differently, the weld pressure applied by the heat die tooling assembly on the front and rear sheets can be measured in terms of combined film thickness compression. The pressure can also be measured in terms of welding die gap. For example, after the heat dies are set to an effective weld starting point with a starting gap therebetween, the gap can decrease about 20% to about 40% of the starting gap, which represents the amount the two films are compressed during welding. In an example, the starting gap can be marked by a point at which the two heat dies contact the two sheets but before moving against or compressing the two sheets. In practice, as the side rails of two heat dies contact one another with the two films to be welded located therebetween, the film compression is automatically performed by pre-configuring the various geometries and weld surfaces of the two heat dies.

The width of a typical perimeter seal can be about 4 mm to about 7 mm with other range contemplated. For example, the top or upper perimeter seal used for hanging the flexible container can be much larger than the width along one of the side edges.

The perimeter seal used for securing the front and rear sheets together can be a permanent seal in that it is not intended for peeling or rupturing compared to peelable seals of multi-compartment flexible containers, which utilize peelable seals to separate the multiple compartments and subsequently allow the peelable seals to be opened to enable mixing of the contents from the previously separated compartments.

Because a perimeter seal can be a permanent seal, when a typical flexible container that is filled with a solution or fluid is dropped from some elevation above the ground and hits the ground, fluid pressure generated inside the container when the container impacts the ground can cause a weak point within the container to fail before the permanent seal fails or can cause the permanent seal to fail. For example, the front and/or rear sheet can burst or rupture, the saddle of the port dispensing system can crack, and/or the one or more nozzles on the dispensing port system can crack before the permanent seal separates. On occasions, the permanent seal can also fail and can allow the contents to spill out.

In accordance with aspects of the present disclosure, a modified perimeter seal, along a cross section, is provided to have at least one of a permanent seal section and a pressure absorbing seal section. The pressure absorbing seal section can release or separate before the front and/or rear sheet ruptures or other parts of the flexible container crack when the container is subjected to an impact. Thus, when a flexible container filled with a liquid or solution and having a perimeter seal of the present disclosure is dropped, the pressure absorbing seal section of the perimeter seal is configured to release, split, rupture, or separate to absorb the impact pressure, thereby eliminating the possibility that other part or parts of the flexible container may rupture or crack due to the impact.

In an example, a perimeter seal of the present comprises a permanent seal section, which is closer to the outer edge of a flexible container, and a pressure absorbing seal section, which is closer to the enclosed space of the container. The term permanent seal section is understood to have a higher rupture point than the pressure absorbing seal section and not necessarily mean unbreakable no matter the applied load, pressure, or circumstances.

The perimeter seal of the present disclosure includes a seal having at least two seal properties or characteristics, such as having at least two different load values. As further discussed below, these at least two different seal properties or characteristics can be load values that mark when the respective seal fails, such as peels or separates. The transition between the permanent seal section and the pressure absorbing seal section may also have a different seal property, such as a different peel point. In yet other examples, the perimeter seal 200 can be configured to have multiple seal properties by modifying the heat dies used to form the perimeter seal.

A perimeter seal of the present disclosure can have both a permanent seal component or section and a pressure absorbing seal component or section. The permanent seal component can be structured to permanently secure the first sheet to the second sheet without peeling or separating due to pressure, by squeezing the flexible container or by dropping the flexible container, or can only separate at a much higher yield point than normal operating conditions and handling. Conversely, the pressure absorbing seal component or section is configured to separate, peel, or rupture due to pressure. If the flexible container is a multi-compartment container and incorporates one or more peelable seals, the pressure absorbing seal component of the perimeter seal can be configured to release or peel before the peelable seal. However, other provisions may be included to enable the absorbing seal to release before the peelable seal, such as by folding the flexible container.

Characteristics, such as load values, of the pressure absorbing seal component or section can be controlled by modifying the pressure applied to the front and rear sheets by the heat die tooling assembly when forming the perimeter seal. In other examples, the weld time or the weld temperature can be modified while maintaining the weld pressure to modify the characteristics of the pressure absorbing seal component or section. In yet other examples and for a given film, two or all three of the parameters, time, temperature, and pressure, can be modified to form the perimeter seal with a permanent seal component or section and a pressure absorbing seal component or section.

A perimeter seal provided herein can have an overall width that is about 6 mm to about 14 mm. In some examples, the width of the permanent seal section can be about 3 mm to about 8 mm and the width of the pressure absorbing seal section can be about 1.5 mm to about 7 mm. Depending on the welding parameters and the film material used, the overall width of the perimeter seal and the width of the permanent seal component and the pressure absorbing seal component can change.

The pressure absorbing seal section can be understood to be formed purposefully after considering one or more of the following parameters: the shape of the heat dies, the container sheet materials, the applied pressure of the heat dies, the heating temperatures of the heat dies, the heating time, and the width of the pressure absorbing seal section, among others. Thus, the pressure absorbing seal section is more than a mere byproduct of a radiused corner incorporated at an edge of a typical heat die, which does not account for the width of the radiused corner compared to the width of a perimeter seal or the inside transition section between the permanent seal and the pressure absorbing seal. Said differently, two head dies combined to form a seal weld between two film layers will not produce the disclosed pressure absorbing seal at the radiused corners of the two heat dies. Among other things, the end edge formed by the radiused corners will not yield the pressure absorbing characteristic of the pressure absorbing seal disclosed herein, as further discussed below.

When a flexible container that is filled with a solution or liquid and having the perimeter seal of the present disclosure is dropped against a hard surface, some to all of the width of the pressure absorbing seal section can separate along the separation line up to, and possibly including, the transition with the permanent seal section to spare other part or parts of the flexible container from cracking, tearing, or rupturing.

In some examples, a perimeter seal, which can have a pressure absorbing seal section, may be applied to the entire outer perimeter of a flexible container or to just a subset or section of the perimeter. For example, a perimeter seal may be applied or practiced for just a first side edge, a second side edge, a bottom edge, a top edge, or to all or some combinations of the noted edges of a flexible container. In still other examples, the perimeter seal may be practiced for only a section or length of any particular edge while a different edge may have the entire length formed with the modified perimeter seal.

A perimeter seal can have an inner edge closest to the enclosed space of the container and an outer edge, further away from the enclosed space. The inner edge can include a first peelable transition or characteristic formed by the inner end corners or radiused corners of the heat dies, as further discussed below.

A second peelable transition or characteristic can be formed between the permanent seal section and the pressure absorbing seal section of the perimeter seal, which transition point can be spaced from the outer edge of the perimeter seal and the first peelable transition. Each peelable transition or characteristic is understood to mark a distinct change and a boundary between two adjacent environments. For example, the first peelable transition marks a change between the enclosed space and the pressure absorbing seal. The second peelable transition marks a change between the pressure absorbing seal section and the permanent seal section. In other examples, as further discussed below, additional peelable transitions may be formed between the first peelable transition and the second peelable transition.

In practice, the first peelable transition may be formed as a byproduct of radiused corners of two heat dies used to form the perimeter seal. However, as conventional heat dies used to form a perimeter seal will only have a permanent seal section, the width formed by the radiused corners of the two heat dies is generally very short or small compared to the pressure absorbing seal section of the present invention and generally will not perform the required pressure absorbing function described herein, which is why prior art flexible containers tend to rupture or fail when accidentally dropped at certain normal working elevations.

Further, conventional heat dies do not produce at least two distinct seal sections when used to form a perimeter seal. In particular, conventional heat dies do not have a pressure absorbing seal section and a permanent seal section, in addition to having a first peelable transition located adjacent an enclosed space and a second transition between a pressure absorbing seal section and a permanent seal section. Still further, conventional heat dies do not generate an inner or second peelable transition that is located further away from the enclosed space and spaced from the first peelable transition and from the outer edge.

A tooling for forming the perimeter seal of the present disclosure can comprise a first heat die and a second heat die configured to form a seal by fusing two film layers located in the space between the two heat dies together. The space between two adjacent weld surfaces of the two heat dies may be referred to as a film welding space. The film welding space at the flat sections of two flat heat dies for forming the permanent seal can have a space or gap of about 0.5 mm to about 1 mm with other ranges contemplated depending on the weld parameters and film materials used.

A first heat die can have a permanent seal welding section with a surface and a pressure absorbing seal welding section with a surface separated from one another by a transition section. A second heat die can have a single characteristic welding section, such as a single generally planar or flat weld section with a weld surface. However, the second heat die is not limited to having only a single characteristic welding section. When the two heat dies are placed in close proximity, such as when forming a perimeter seal for two film layers, a variable gap is defined by the surfaces of the two heat dies of the present disclosure. This variable gap can be utilized to exert different weld pressure along the width of the heat die tooling on the two film layers to form a perimeter seal having both a permanent seal section and a pressure absorbing seal section. This variable gap is distinctive and is more than a mere byproduct of radiused corners of prior art heat dies, which are typically present at two far ends only. The variable gap of the present invention spans across a defined width and within that variable gap, a permanent seal section and a pressure absorbing seal section can be formed.

If a planar surface of a perimeter seal welding section a of a first heat die defines a reference plane, then the surface of the pressure absorbing seal welding section, for example at or near an outer surface edge, can be offset from the reference plane by about 0.025 mm to about 0.26 mm. This offset may be referred to as an offset seal gap. In a particular example, the offset seal gap can be about 0.1 mm to about 0.16 mm. When two plates are combined, the total offset seal gap can be about 0.05 mm to 0.32 mm, which is in addition to the typical permanent seal gap between two planar heat dies of about 0.5 mm to about 1 mm.

In an example, a perimeter seal having both a permanent seal section and a pressure absorbing seal section can be formed in a single weld step. For example, when a tooling with two weld plates is placed against two film layers, a perimeter seal having both a permanent seal section and a pressure absorbing seal section can be formed by the perimeter seal welding section and the pressure absorbing seal welding section of the first heat die opposing the second heat die. The second heat die can have a single planar surface. Thus, two separate weld steps, one to form the permanent seal section and another to form the pressure absorbing seal section, can be avoided, although such process is contemplated for producing a perimeter seal having both a permanent seal section and a pressure absorbing seal section of the present disclosure.

A tooling in which one of two heat dies can have a single characteristic welding section, as opposed to both heat dies having two or more unique weld surfaces, is advantageous in that alignment between the two heat dies can be practically eliminated since curve surfaces or modified surface features of two different heat die surfaces are not utilized, thus eliminating the need for accurate alignment of curved or modified surface features from two different heat dies.

In an example, a pressure absorbing seal section of a perimeter seal can have a separation characteristic that is lower than a separation characteristic of a permanent seal section. In other words, if the separation characteristic of the permanent seal section, or a point at which the permanent seal section separates, is X, which can be measured in force, then the separation characteristic of the pressure absorbing seal section can be Y, wherein X is greater than Y.

In some examples, a permanent seal section does not separate or separates at a much higher value than the rupture value of the front and/or rear sheet. Thus, when a bag is dropped or purposefully squeezed, the pressure absorbing seal section of the perimeter seal can have a separation characteristic that is lower than the rupture point of the front sheet, the rear sheet, or both the front sheet and the rear sheet, and lower than the separation value of the permanent seal. In practice, the permanent seal section tends to fail or rupture before the front, rear, or both the front and rear sheets of the flexible container rupture or fail.

In an example, when a flexible container having a perimeter seal of the present disclosure along at least one container edge is dropped from a working height, one of the following scenarios can occur along a weld section of the perimeter seal: (1) some or all of the width of the pressure absorbing seal section of the perimeter seal fails and none of the width of the permanent seal section fails or (2) all of the width of the pressure absorbing section of the perimeter seal fails and some of the width of the permanent seal section fails. Under different circumstances, such as when the bag is stepped on, the perimeter seal can fail differently.

Different embodiments of different heat die tooling assemblies usable for forming a perimeter seal of the present disclosure are included within the scope of the present invention. Flexible containers formed using heat die tools of the present disclosure are also within the scope of the present invention. In the various alternative embodiments, the first heat die can incorporate an absorbing seal weld section, or pressure absorbing seal welding section, with a surface that is shaped differently than the pressure absorbing seal welding section of the first heat die of the first embodiment to produce a pressure absorbing seal section that has a different peel or separation characteristic than the pressure absorbing seal section formed by the tooling used to make the perimeter seal of the first embodiment.

In the first embodiment, a first heat die with an absorbing weld section or pressure absorbing seal welding section has a generally planar or constant surface area. In an alternative embodiment, the pressure absorbing seal welding section of the first heat die has a surface with a constant slope. In other examples, the slope can be a complex slope. The transition section between the permanent seal welding section and the pressure absorbing seal welding section can have a surface with a steeper slope than the slope of the pressure absorbing seal welding section.

In another embodiment, a first heat die with a pressure absorbing seal welding section with a surface that extends directly from the permanent seal welding section without a pronounced transition section can be incorporated. Said differently, the surface of the transition section of the present embodiment can have a same slope as the slope of at least part of the planar welding surface of the pressure absorbing seal welding section.

In another embodiment, a pressure absorbing seal welding section of a first heat die has undulating weld surfaces that define a variable gap with varying pockets having different gaps disposed between smaller gap sections. The transition section between the permanent seal welding section and the pressure absorbing seal welding section can have a steeper slope than the slope of the pressure absorbing seal weld section.

In yet another example, a pressure absorbing seal welding section of a first heat die has undulating weld surfaces that define a variable gap with a series of interconnecting jagged tooth to form a saw-teeth like pressure absorbing weld section. The transition section between the permanent seal welding section and the pressure absorbing seal welding section can have a steeper slope than the slope of the pressure absorbing seal weld section.

In other alternative heat weld tooling embodiments, both the first heat die and the second heat die incorporate a permanent seal welding section and a pressure absorbing seal welding section. The two heat dies of each tooling can be the same with the same permanent seal weld section and pressure absorbing seal weld section but arranged differently or can be different.

An exemplary heat die, which may also be referred to as a weld plate or hot weld plate, can comprise a plate body comprising two elongated perimeter rails. The two perimeter rails can define two side edges and at least part of two end edges of the plate body. The two perimeter rails can each have a length and a thickness or height, which is orthogonal to the length. The two perimeter rails can function as stop platforms when two heat dies are stacked, such as with two film layers located therein for welding, and surfaces of the perimeter rails from the two heat dies contact one another. A gap or space is provided in between for welding two film layers together to from a perimeter seal for a flexible container.

Each of the two perimeter rails can include one or more alignment bosses. The alignment bosses can be located near the corresponding intersections of the side edges and the end edges. Each perimeter rail can incorporate two alignment bosses. In use, two mating weld plates can align and can have their welding surfaces aligned via placement of dowels or pins through the alignment bosses of the stacked weld plates to align the weld surfaces for welding the film layers, which can be a single ply film or a multi-laminate film.

A central weld body section is located between the two perimeter rails. A perimeter weld element is disposed at the central weld body section and is spaced from the two perimeter rails by two gaps. In an example, the perimeter weld element has two side weld elements, and two end weld elements, which can be referred to as a first end weld element and a second end weld element, respectively.

The two side weld elements can be formed contiguously or continuously, such as without a break or a gap, with the first end weld element. Voids can be provided in parts or sections of the perimeter weld element. The voids can be incorporated where the size or thickness of the perimeter seal is to be adjusted, such as by using the voids rather than the entire area as a seal so as to minimize the overall seal width. In some examples, at least part of the second end weld element can be formed contiguously or continuously with the two side weld elements. A gap or empty area can be provided at the second end weld element.

When two weld plates are used to form a perimeter seal around two film layers, the gaps at the second end weld elements of the two weld plates can leave a path or passage in the perimeter seal of the flexible container. The path or passage can then be used to fill the flexible container with a content, such as with a fluid. After the fill step, a saddle of a dispensing port system can be inserted and rest of the perimeter seal completed.

In some examples, the two gaps at the second end weld elements of the two weld plates can be sized and shaped to receive a dispensing port system to weld the dispensing port system to the flexible container at the same time the perimeter seal is formed. The first end or the opposite end of the dispensing port system can be left partially open or completely open, such as un-sealed, for purposes of filling the contents of the flexible container. The un-sealed end can subsequently be sealed after filling the contents of the flexible container. In an example, the sealed end opposite the dispensing port system can be provided with an enlarged perimeter seal and can include a perimeter defining a hole for hanging the flexible container. When a particular heat die incorporates a gap along the perimeter weld element, the gap allows an edge of a container formed thereby to be further manipulated, such as to be filled with a fluid. The open edge can subsequently be closed using another or a different set of heat dies.

A plurality of equally spaced or randomly spaced purging orifices may be provided within the boundary defined by the perimeter weld element. The spaced purging orifices allow trapped air to be purged or discharged during the heat welding procedure. In some examples, equally spaced or randomly spaced purging orifices can also be provided through the central weld body section outside of the boundary defined by the perimeter weld element to similarly allow trapped air to be purged.

The height or thickness of the perimeter rail measured from the inside surface to the exterior weld plate surface is greater than the height or thickness measured from the weld surface of the perimeter weld element to the exterior weld plate surface. The height difference or offset defines the film welding space or gap previously discussed. Said differently, when two weld plates are stacked, the two plates contact one another at the respective inside surfaces of the perimeter rails. The offset gap at the two weld surfaces of the two perimeter weld elements define the film welding space for welding the permanent seal section and the pressure absorbing seal section of the perimeter seal.

In an example, the pressure absorbing seal welding section can be a simple tapered or inclined surface, which can resemble the pressure absorbing seal welding section of FIG. 6C. However, the pressure absorbing seal welding section is not limited and can embody any of the pressure absorbing seal welding sections described elsewhere herein.

When a perimeter seal having both a permanent seal section and a pressure absorbing seal section of the present invention is subjected to a pull test and graphed on a Load to Peel extension graph, the graph describes an increasing slope, followed by a peak, followed by a decreasing slope, followed by an increasing slope, followed by a second peak, which is higher than the first peak, and then followed by a final decreasing slope.

The second peak region can be indicative of the fail point of the test sample, which can be considered the point when the permanent seal section fails by peeling or separating or the failure of at least one of the front and rear sheets, which can rupture or split.

The first peak followed by a decreasing slope on the load to peel extension graph demonstrate that the perimeter seal having both a pressure absorbing seal section and a permanent seal section may not peel or fail at the permanent seal section until after the pressure absorbing seal section of the permanent seal separates or fails. In particular examples, the permanent seal section of the perimeter seal may not peel or fail at least until after the load on the permanent seal section increases. If the permanent seal section does separate or fail, the load value of the permanent seal can follow by a decrease in value.

Methods of making and of using the flexible containers as described elsewhere herein are within the scope of the present invention.

Other aspects of the present disclosure are described herein below and as shown in the included drawing figures.

BRIEF DESCRIPTION OF THE DRAWINGS

The various embodiments of the present flexible containers, systems, and associated methods now will be discussed in detail with an emphasis on highlighting the advantageous features. These embodiments depict the novel and non-obvious flexible containers, systems and related methods shown in the accompanying drawings, which are for illustrative purposes only. These drawings include the following figures, in which like numerals indicate like parts:

FIG. 1 is a schematic view of a single compartment flexible container comprising two ports.

FIG. 2 is a schematic view of a flexible container comprising multiple compartments, including an empty outlet compartment.

FIG. 3 is a schematic view of a flexible container comprising multiple compartments.

FIG. 4 is a schematic cross-sectional end view of the flexible container of FIG. 1 taken at section A, showing a perimeter seal.

FIG. 5 is an alternative a cross-sectional end view of a perimeter seal with rupture absorbing seal component.

FIGS. 6A-6E are schematic views showing different heat die tooling assemblies usable to make different perimeter seal embodiments with rupture absorbing seal components.

FIGS. 7A-7B are schematic views showing yet additional heat die tooling assemblies usable to make different perimeter seal embodiments with rupture absorbing seal components.

FIG. 8 is a schematic view showing yet another heat die tooling assembly usable to make different perimeter seal embodiments with rupture absorbing seal components.

DETAILED DESCRIPTION

Figure 9A:
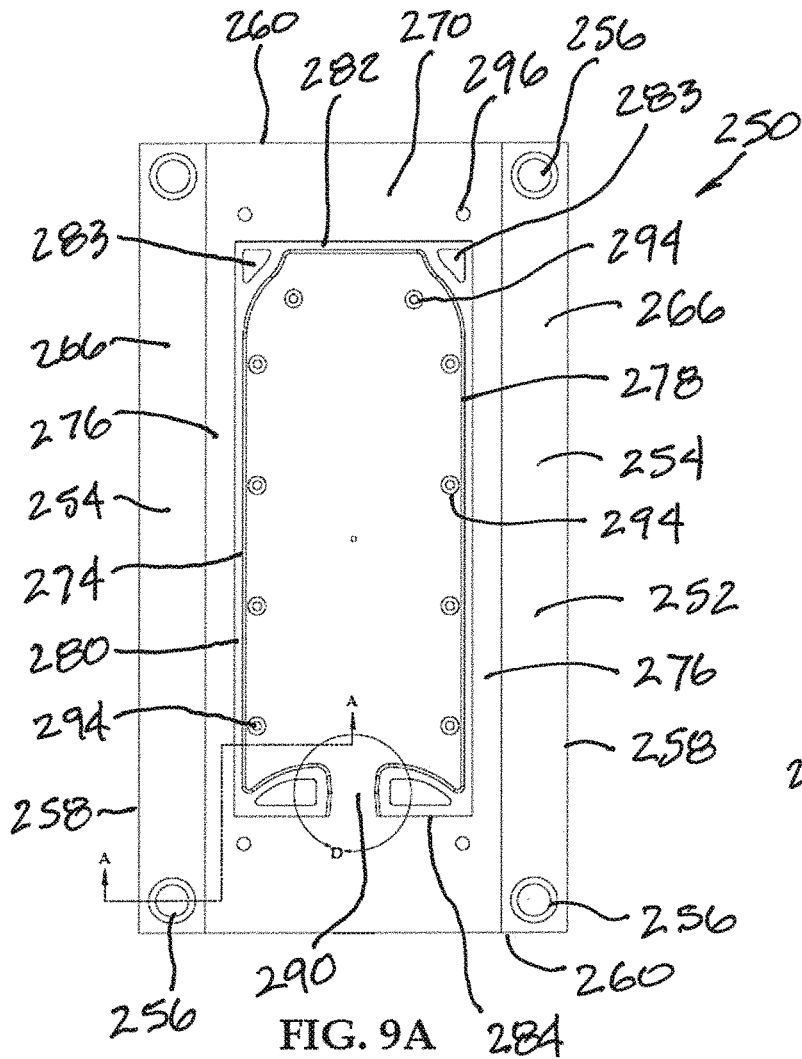
FIG. 9A is a top plan view of an exemplary heat die for use with another heat die to form a perimeter seal embodiment with rupture absorbing seal component and permanent seal component.

The embodiments of the present containers, systems, and associated methods are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unit or a unitary piece and whereas a unitary piece means a singularly formed single piece, such as a singularly formed mold or cast. Still further, the terms "first" and "second" used herein are understood as identifiers only to distinguish between different components but not structurally distinguishing unless the context indicates otherwise. Thus, unless the context indicates otherwise, "first" and "second" are not limiting terms.

With reference now to FIG. 1, a schematic front view of a flexible container 100 provided in accordance with aspects of the present devices, systems, and methods is shown, which can be sized and shaped to accommodate a wide range of available volumetric requirements. The flexible container 100 may be formed by attaching a flexible front or first sheet 102 to a flexible rear or second sheet 104 and sealing the perimeter 106 of the two sheets with a perimeter seal 108. For discussion purposes, the container perimeter 106 is understood to include a first side edge 110, a second side edge 112, a bottom or lower edge 114, and a top or upper edge 116, elevation-wise. The perimeter seal 108 can be formed as a permanent seal in that the seal 108 is not intended to be separable or peelable without tearing the front 102 and/or rear 104 sheets. The perimeter seal 108 along the edges therefore include a first side permanent seal 120, a second side permanent seal 122, a bottom or lower permanent seal 124, and a top or upper permanent seal 126.

In some examples, the upper permanent edge seal 126 can be wider than the lower permanent edge seal 124 and/or the two side permanent seals 120, 122. The wider upper permanent edge seal 126 provides room or space to incorporate a perimeter 130 defining a hole for use with a hook to hang the flexible container 100, such as for dispensing or for displaying. Optionally, a dispensing port system 134 can be provided with the bottom permanent seal 124, such as placed between the front and rear sheets 102, 104 and then heat sealed to the front and rear sheets 102, 104 to dispense fluid or contents from the enclosed space 132 within the container 100 along the bottom edge 114. The dispensing port system 134 has a saddle 136, a first port or nozzle 138 and second port or nozzle 140. Optionally, only one port is included. Still further, the port system 134 may be omitted altogether and the flexible container 100 is provided with a weakened section, such as a puncture site, for puncturing using a straw or the like to facilitate dispensing the contents from the enclosed space 132. Terminal ends may be welded to the first and second ports for use with administrative tubing sets, such as an IV spike or drip line. The terminal ends, when used, may include a septum or a piston forming a needleless connector.

In an example, the flexible container 100 may be made from the same materials using the same methods as disclosed in U.S. Pat. No. 4,803,102 to Raniere et al. and the two ports may be provided with end fittings or caps for use as a fill port, a drain port, or an additive port. The front and rear sheets 102, 104 of the flexible container 100 can each be a monolayer film or single ply film, can each be a multi-laminate film having multiple layers, or can be one of each, a monolayer film and a multi-laminate film. The two sheets can also be formed by taking a single elongated sheet and folding the single sheet to form two overlapping layers having a fold line and then sealing the open sides to form an enclosed space.

Any number of conventional monolayer films and multi-laminate films may be used to practice the container with perimeter seals with rupture absorbing seal components of the present disclosure. In an example, the films used to make the flexible container of the present disclosure can be one of various films disclosed in U.S. Pat. Nos. 4,803,102; 5,910, 138; 5,928,213; 5,944,709; 6,165,161 and 6,203,535, the contents of each of which are expressly incorporated herein by reference. For example, the monolayer film material can be a polypropylene-based material. It is typical to mix or compound elastomeric materials in the base polypropylene to obtain more flexible properties. The front and rear films of the flexible container can be the same or can be different.

When using a multilayer film, the multilayer film can be a polypropylene (PP)-based material. Each layer of the multi-layer film can have different properties, such as an outer layer that has a higher melting point to facilitate printing thereon and is less prone to sticking to heated tooling, an inner layer that bonds well to the mating film and ports yet has properties that allow for peelable-seals, and an inner layer that facilitates the barrier properties to prevent moisture loss. The front and rear films of the flexible container can be the same or can be different. One of the layers of the multi-layer film can include an opaque layer, such as an aluminum layer, to minimize UV light penetrating the contents of the flexible container. In a particular example, a PP-based multilayer film is used to form a flexible container or bag. The PP-based flexible container may be formed using the same PP-based material as the commercially available EXCEL® IV container. The flexible container can have one of the following standard sizes: 250 mL, 500 mL, and 1000 mL. In other examples, the flexible container can have other sizes.

FIG. 2 shows a flexible container 150 with multiple compartments including an upper or first compartment 152, an intermediate or second compartment 154, and an outlet or third compartment 156. A dispensing port system 134 is in fluid communication with the outlet compartment 156. The upper compartment 152 and the intermediate compartment 154 are separated from one another by a first peelable seal 160 that is designed to rupture or separate and the intermediate compartment 154 is separated from the outlet compartment 156 by a second peelable seal 162, which is also design to peel or separate upon application of pressure. An optional opaque protective cover 170 with a pull tab 172 extending or hanging from the cover can be applied to the outer surface of the intermediate compartment 154 to provide extra protection, such as from light or moisture, for the contents inside the intermediate compartment, which can contain a medicament. The first compartment 152 can contain a liquid diluent. The outlet or third compartment 156 can be an empty compartment to enable further mixing of the first two compartments 152, 154 prior to dispensing the mixed solution out the dispensing port system 134.

Prior to using the flexible container 150, the opaque protective cover 170 can be removed, or partially lifted, by pulling on the pull tab 172 to allow observation of the contents within the intermediate compartment 154, which can be a liquid or powder medicament. The flexible container 150 can have a similar perimeter seal 108 as the flexible container 100 of FIG. 1.

FIG. 3 shows yet another flexible container 180 in accordance with further aspects of the present disclosure. The container 180 of FIG. 3 is similar to the container of FIG. 2 with the exception of having only two compartments instead of three compartments. Thus, the compartment 152 further away from the dispensing system 134 can be called a first compartment and the compartment 152 closer to the dispensing system 134 can be called a second compartment. For example, the empty outlet compartment can be omitted. Further, while a protective cover 170 is shown with a pull tab 172, such additional protective cover can be omitted.

In some examples, the containers 100, 150, 180 described herein are provided without any dispensing port or provided with a dispensing port system having just one port or more than two ports. The various containers disclosed herein may be used for any number of applications, including for drinks, dietary applications, irrigation applications, and nutritional applications, among others.

With reference now to FIG. 4, a partial cross-sectional end view of section A of FIG. 1 is shown. The features represented by section A may be incorporated with any of the containers described herein. As shown, the section comprises a front sheet 102 and a rear sheet 104 joined to one another by a perimeter seal 108, which can be a first edge seal 120. The perimeter seal 108 can also be used for the second edge seal 122, the upper perimeter seal 126, the bottom perimeter seal 124 or for all the perimeter seals. Also partially shown is the enclosed space 132 defined by the front and rear sheets. Along the outer edge 186 of the perimeter seal 108 opposite the enclosed space 132, is an overhang 188, which shows remnants of the front and rear sheets that have not been trimmed or have not been sealed-in to form part of the perimeter seal 108. Optionally, the overhang 188 can be eliminated by trimming using any commercially available trimming means and the perimeter seal 108 terminates at the outer edge 186, without the overhang.

The perimeter seal 108 may be formed by applying the front and rear sheets 102, 104 between two heat dies and then pressing the heat dies together under a predetermined pressure, for a predetermined time, and heating the heat dies to a predetermined temperature to melt the inner most layers to then fuse the inner surfaces of the two layers 102, 104 together to form the seal 108. The time, temperature, and pressure utilized in the welding step can depend on the materials used for the front and rear sheets, the thickness of the front and rear sheets, the type of layers if a multi-layer film, and the thickness of the inner most layers that contact one another. For a polypropylene-based material, seal parameters of approximately 260° F.-310° F. and for about 0.5 sec to 2.0 sec can be used with heat dies to form the perimeter seals. The weld pressure applied by the heat dies on the front and rear sheets 102, 104 can be the equivalent of compressing the two films 102, 104 approximately 15% to about 45% of the combined film thickness. Said differently, the weld pressure applied by the heat die tooling assembly on the front and rear sheets can be measured in terms of combined film thickness compression. The pressure can also be measured in terms of welding die gap. For example, after the heat dies are set to an effective weld starting point with a starting gap therebetween, the gap can decrease about 20% to about 40% of the starting gap. In an example, the starting gap can be marked by a point at which the two heat dies contact the two sheets but before moving against or compressing the two sheets. In practice, as the side rails of two heat dies contact one another with the two films to be welded located therebetween, the film compression is automatically performed by pre-configuring the various geometries and weld surfaces of the two heat dies, as further discussed below with reference to FIG. 9A.

The width of a typical perimeter seal 108 can be about 4 mm to about 7 mm with other range contemplated. For example, the top or upper perimeter seal used for hanging the flexible container can be much larger than the width along one of the side edges. As previously alluded to, the perimeter seal 108 can be a permanent seal in that it is not intended for peeling or rupturing compared to the peelable seals 160, 162 of the multi-compartment flexible container 150 of FIG. 2. Because the perimeter seal 108 can be a permanent seal, when a flexible container that is filled with a solution or fluid is dropped from some elevation above the ground and hits the ground, fluid pressure generated inside the container when the container impacts the ground can cause a weak point within the container to fail before the permanent seal fails or can cause the permanent seal to fail. For example, the front and/or rear sheet can burst or rupture, the saddle of the port dispensing system can crack, and/or the one or more nozzles on the dispensing port system can crack before the permanent seal separates. In accordance with aspects of the present disclosure, a modified perimeter seal, along a cross section, is provided to have at least one of a permanent seal section and a pressure absorbing seal section that can release before the front and/or rear sheet ruptures or other parts of the flexible container crack. Thus, when a flexible container filled with a liquid or solution and having a perimeter seal of the present disclosure is dropped, the pressure absorbing seal section of the perimeter seal is configured to release, split, rupture, or separate to absorb the impact pressure, thereby eliminating the possibility that other part or parts of the flexible container may rupture or crack due to the impact.

With reference now to FIG. 5, a cross-sectional end view of a perimeter seal that is similar to the perimeter seal 108 of FIG. 4 is shown. In the present embodiment, the perimeter seal 200 is modified to include a permanent seal section 202, which is closer to the outer edge of the container, and a pressure absorbing seal section 204, which is closer to the enclosed space 132 of the container. The perimeter seal 200 of the present disclosure therefore includes a seal having at least two seal properties or characteristics. As further discussed below, these at least two different seal properties or characteristics can be load values that mark when the respective seal fails, such as peels or separates. The transition between the permanent seal section 202 and the pressure absorbing seal section 204 may also have a different seal property, such as a different peel point. In yet other examples, the perimeter seal 200 can be configured to have multiple seal properties by modifying the heat dies used to form the perimeter seal.

As shown in FIG. 5, the perimeter seal 200 has both a permanent seal component or section 202 and a pressure absorbing seal component or section 204. The permanent seal component 202 is structured to permanently secure the first sheet 102 to the second sheet 104 without peeling or separating due to pressure, by squeezing the flexible container or by dropping the flexible container. Conversely, the pressure absorbing seal component or section 204 is configured to separate, peel, or rupture due to pressure. If the flexible container is a multi-compartment container and incorporates one or more peelable seals, the pressure absorbing seal component 204 of the perimeter seal is configured to release or peel before the peelable seal. However, other provisions may be included to enable the absorbing seal to release before the peelable seal, such as by folding the flexible container.

Characteristics, such as load values, of the pressure absorbing seal component or section 204 can be controlled by modifying the pressure applied to the front and rear sheets by the heat die tooling assembly when forming the perimeter seal 200. In other examples, the weld time or the weld temperature is modified while maintaining the weld pressure to modify the characteristics of the pressure absorbing seal component or section 204. In yet other examples and for a given film, two or all three of the parameters, time, temperature, and pressure, are modified to form the perimeter seal with a permanent seal component or section 202 and a pressure absorbing seal component or section 204.

As shown in FIG. 5, the perimeter seal 200 can have an overall width that is about 6 mm to about 14 mm. In some examples, the width of the permanent seal section 202 can be about 3 mm to about 8 mm and the width of the pressure absorbing seal section 204 can be about 1.5 mm to about 7 mm. Depending on the welding parameters and the film material used, the overall width of the perimeter seal 200 and the width of the permanent seal component 202 and the pressure absorbing seal component 204 can change.

The pressure absorbing seal section 204 can be understood to be formed purposefully after considering one or more of the following parameters: the shape of the heat dies, the container sheet materials, the applied pressure of the heat dies, the heating temperatures of the heat dies, the heating time, and the width of the pressure absorbing seal section, among others. Thus, the pressure absorbing seal section 204 is more than a mere byproduct of a radiused corner incorporated at an edge of a typical heat die, which does not account for the width of the radiused corner compared to the width of a perimeter seal or the inside transition section between the permanent seal and the pressure absorbing seal. Said differently, two head dies combined to form a seal weld between two film layers will not produce the disclosed pressure absorbing seal at the radiused corners of the two heat dies. Among other things, the end edge formed by the radiused corners will not yield the pressure absorbing characteristic of the pressure absorbing seal disclosed herein, as further discussed below.

When a flexible container that is filled with a solution or liquid and having the perimeter seal 200 of the present disclosure is dropped against a hard surface, some to all of the width of the pressure absorbing seal section 204 can separate along the separation line 210 up to, and possibly including, the transition with the permanent seal section 202 to spare other part or parts of the flexible container from cracking, tearing, or rupturing.

In some examples, the perimeter seal 200 of FIG. 5, which has a pressure absorbing seal section, may be applied to the entire outer perimeter 106 (FIG. 1) of a flexible container or to just a subset or section of the perimeter. For example and with reference to FIG. 1, the perimeter seal 200 of FIG. 5 may be applied or practiced for just the first side edge 110, the second side edge 112, to the bottom edge 114, the top edge 116, or to all or some combinations of the noted edges. In still other examples, the perimeter seal 200 of FIG. 5 may be practiced for only a section or length of any particular edge while a different edge may have the entire length formed with the modified perimeter seal.

With continued reference to FIG. 5, the perimeter seal 200 has an inner edge 190 closest to the enclosed space 132 and an outer edge 186, further away from the enclosed space. The inner edge 190 can include a first peelable transition or characteristic 192a formed by the inner end corners or radiused corners of the heat dies, as further discussed below.

A second peelable transition or characteristic 192b can be formed between the permanent seal section 202 and the pressure absorbing seal section 204 of the perimeter seal 200, which transition point is spaced from the outer edge 186 of the perimeter seal and the first peelable transition 192a. Each peelable transition or characteristic is understood to mark a distinct change and a boundary between two adjacent environments. For example, the first peelable transition 192a marks a change between the enclosed space 132 and the pressure absorbing seal 204. The second peelable transition 192b marks a change between the pressure absorbing seal section 204 and the permanent seal section 202. In other examples, as further discussed below, additional peelable transitions may be formed between the first peelable transition 192a and the second peelable transition 192b.

In practice, the first peelable transition 192a may be formed as a byproduct of radiused corners of two heat dies used to form the perimeter seal 200. However, as conventional heat dies used to form a perimeter seal will only have a permanent seal section, the width formed by the radiused corners of the two heat dies is generally very short or small compared to the pressure absorbing seal section 204 of the present invention and generally will not perform the required pressure absorbing function described herein, which is why prior art flexible containers tend to rupture or fail when accidentally dropped at certain normal working elevations.

Further, conventional heat dies do not produce at least two distinct seal sections when used to form a perimeter seal. In particular, conventional heat dies do not have a pressure absorbing seal section and a permanent seal section, in addition to having a first peelable transition located adjacent an enclosed space and a second transition between a pressure absorbing seal section and a permanent seal section. Still further, conventional heat dies do not generate an inner or second peelable transition 192b that is located further away from the enclosed space 132 and spaced from the first peelable transition 192b and from the outer edge 186.

With reference now to FIG. 6A, a schematic depiction of an end cross-section of a tooling 220 for forming the perimeter seal 200 of the present disclosure, such as the perimeter seal 200 of FIG. 5, is shown. The tooling 220 comprises a first heat die 222 and a second heat die 224 configured to form a seal by fusing two film layers located in the space 226 between the two heat dies 222, 224 together. The space 226 between the two heat dies may be referred to as a film welding space. The film welding space at the flat sections of two flat heat dies for forming the permanent seal can have a space or gap of about 0.5 mm to about 1 mm with other ranges contemplated depending on the weld parameters and film materials used.

As shown, the first heat die 222 has a permanent seal welding section 230 with a surface and a pressure absorbing seal welding section 232 with a surface separated from one another by a transition section 234. The second heat die 224 can have a single characteristic welding section, such as a single generally planar or flat weld section. However, the second heat die 224 is not limited to having only a single characteristic welding section. When the two heat dies 222, 224 are placed in close proximity, such as when forming a perimeter seal for two film layers, a variable gap 228 is defined by the surfaces of the two heat dies. This variable gap 228 can be utilized to exert different weld pressure along the width of the heat die tooling on the two film layers to form a perimeter seal 200 having both a permanent seal section 202 and a pressure absorbing seal section 204 (FIG. 5). This variable gap 228 is distinctive and is more than a mere byproduct of radiused corners of prior art heat dies, which are typically present at two far ends only. The variable gap 228 of the present invention spans across a defined width and within that variable gap, a permanent seal section and a pressure absorbing seal section can be formed.

Again referring to FIG. 6A, if the planar surface of the perimeter seal welding section 230 of the first heat die 222 defines a reference plane, then the surface of the pressure absorbing seal welding section 232, for example at or near the outer surface edge 232a, can be offset from the reference plane by about 0.025 mm to about 0.26 mm. This offset may be referred to as an offset seal gap. In a particular example, the offset seal gap can be about 0.1 mm to about 0.16 mm. When two plates are combined, the total offset seal gap can be about 0.05 mm to 0.32 mm, which is in addition to the typical permanent seal gap between two planar heat dies of about 0.5 mm to about 1 mm.

In an example, the perimeter seal 200 having both a permanent seal section 202 and a pressure absorbing seal section 204 can be formed in a single weld step. For example, when the tooling 220 of FIG. 6A is placed against two film layers, a perimeter seal 200 having both a permanent seal section 202 and a pressure absorbing seal section 204 is formed by the perimeter seal welding section 230 and the pressure absorbing seal welding section 232 of the first heat die 222 opposing the second heat die 224. The second heat die 224 can have a single planar surface. Thus, two separate weld steps, one to form the permanent seal section and another to form the pressure absorbing seal section, can be avoided, although such process is contemplated for producing a perimeter seal 200 having both a permanent seal section 202 and a pressure absorbing seal section 204 of the present disclosure.

The tooling 220 of FIG. 6A in which the second heat die 224 has a single characteristic welding section is advantageous in that alignment between the two heat dies can be practically eliminated since curve surfaces or modified surface features of two different heat die surfaces are not utilized, thus eliminating the need for accurate alignment of curved or modified surface features from two different heat dies. In an example, the pressure absorbing seal section of the perimeter seal has a separation characteristic that is lower than the separation characteristic of the permanent seal section. In other words, if the separation characteristic of the permanent seal section, or a point at which the permanent seal separates, is X, which can be measured in force, then the separation characteristic of the pressure absorbing seal section can be Y, and where in X is greater than Y.

In some examples, the permanent seal section 202 does not separate or separates at a much higher value than the rupture value of the front and/or rear sheet. Thus, when a bag is dropped or purposefully squeezed, the pressure absorbing seal section 204 of the perimeter seal 200 can have a separation characteristic that is lower than the rupture point of the front sheet, the rear sheet, or both the front sheet and the rear sheet, and lower than the separation value of the permanent seal 202. In practice, the permanent seal section 202 tends to fail or rupture before the front, rear, or both the front and rear sheets of the flexible container rupture or fail.

In an example, when a flexible container having a perimeter seal 200 of the present disclosure along at least one container edge is dropped from a working height, one of the following scenarios can occur along a weld section of the perimeter seal 200: (1) some or all of the width of the pressure absorbing seal section 204 of the perimeter seal 200 fails and none of the width of the permanent seal section 202 fails or (2) all of the width of the pressure absorbing section 204 of the perimeter seal 200 fails and some of the width of the permanent seal section 202 fails. Under different circumstances, such as when the bag is stepped on, the perimeter seal 200 can fail differently.

FIGS. 6B-6E show different embodiments of heat die tooling assemblies usable for forming a perimeter seal 200 (FIG. 5) of the present disclosure. In the various alternative embodiments of FIGS. 6B-6E, the first heat die 222 incorporates an absorbing weld section, or pressure absorbing seal welding section, 232 with a surface that is shaped differently than the pressure absorbing seal welding section 232 of the first heat die 222 of FIG. 6A to produce a pressure absorbing seal section 204 (FIG. 5) that has a different peel or separation characteristic than the pressure absorbing seal section 204 formed by the tooling used to make the perimeter seal 200 of FIG. 6A.

FIG. 6A shows a first heat die 222 with an absorbing weld section or pressure absorbing seal welding section 232 having a generally planar or constant surface area. In FIG. 6B, the pressure absorbing seal welding section 232 of the first heat die 222 has a surface with a constant slope. In other examples, the slope can be a complex slope. The transition section 234 between the permanent seal welding section 230 and the pressure absorbing seal welding section 232 can have a surface with a steeper slope than the slope of the pressure absorbing seal welding section 232.

FIG. 6C shows a first heat die 222 with a pressure absorbing seal welding section 232 with a surface that extends directly from the permanent seal welding section 230 without a transition section, compared to the transition section 234 of FIGS. 6A and 6B. Said differently, the surface of the transition section 234 of the present embodiment has the same slope as the slope of at least part of the planar welding surface of the pressure absorbing seal welding section 232.

FIG. 6D shows a pressure absorbing seal welding section 232 of the first heat die 222 having undulating weld surfaces that define a variable gap 228 with varying pockets having different gaps disposed between smaller gap sections. The transition section 234 between the permanent seal welding section 230 and the pressure absorbing seal welding section 232 can have a steeper slope than the slope of the pressure absorbing seal weld section 232.

FIG. 6E shows a pressure absorbing seal welding section 232 of the first heat die 222 having undulating weld surfaces that define a variable gap 228 with a series of interconnecting jagged tooth to form a saw-teeth like pressure absorbing weld section. The transition section 234 between the permanent seal welding section 230 and the pressure absorbing seal welding section 232 can have a steeper slope than the slope of the pressure absorbing seal weld section 232.

FIGS. 7A and 7B show alternative heat weld tooling embodiments in which each of the first heat die 222 and the second heat die 224 incorporates a permanent seal welding section 230 and a pressure absorbing seal welding section 232. The two heat dies 222, 224 of each tooling 220 can be the same (FIG. 7B) with the same permanent seal weld section and pressure absorbing seal weld section but arranged differently or can be different (FIG. 7A).

FIG. 8 shows an alternative heat weld tooling embodiment 220 in which the transition section 234 between the permanent seal welding section 230 and the pressure absorbing seal weld 232 section has a stepped feature or profile.

With reference now to FIG. 9A, an exemplary heat die 250 in accordance with aspects of the present invention is shown. The heat die 250, which may also be referred to as a weld plate or hot weld plate, comprises a plate body 252 comprising two elongated perimeter rails 254, 254. The two perimeter rails 254, 254 can define two side edges 258, 258 and at least part of two end edges 260, 260 of the plate body 252. The two perimeter rails 254, 254 can each have a length and a thickness or height, which is orthogonal to the length. The two perimeter rails 254, 254 can function as stop platforms 266, 266 when two heat dies 250 are stacked, such as with two film layers located therein for welding, and surfaces of the perimeter rails 254, 254 from the two heat dies contact one another. A gap or space is provided in between for welding two film layers together to from a perimeter seal for a flexible container.

Each of the two perimeter rails 254, 254 can include one or more alignment bosses 256. The alignment bosses can be located near the corresponding intersections of the side edges 258, 258 and the end edges 260, 260. As shown, each perimeter rail incorporates two alignment bosses 256, 256. In use, two mating weld plates 250, 250 can align and can have their welding surfaces aligned via placement of dowels or pins through the alignment bosses 256 of the stacked weld plates to align the weld surfaces for welding the film layers, which can be a single ply film or a multi-laminate film.

A central weld body section 270 is located between the two perimeter rails 254 254. A perimeter weld element 274 is disposed at the central weld body section 270 and is spaced from the two perimeter rails 254, 254 by two gaps 276, 276. In an example, the perimeter weld element 274 has two side weld elements 278, 280, and two end weld elements 282, 284, which can be referred to as a first end weld element 282 and a second end weld element 284, respectively. As shown, the two side weld elements 278, 280 can be formed contiguously or continuously, such as without a break or a gap, with the first end weld element 282. Voids 283 can be provided in parts or sections of the perimeter weld element 274. The voids 283 can be incorporated where the size or thickness of the perimeter seal is to be adjusted, such as by using the voids rather than the entire area as a seal so as to minimize the overall seal width. In some examples, at least part of the second end weld element 284 can be formed contiguously or continuously with the two side weld elements 278, 280. A gap or empty area can be provided at the second end weld element 184.

When two weld plates 250 as shown in FIG. 9A are used to form a perimeter seal around two film layers, the gaps 290 at the second end weld elements 284, 284 of the two weld plates can leave a path or passage in the perimeter seal of the flexible container. The path or passage can then be used to fill the flexible container with a content, such as with a fluid. After the fill step, a saddle of a dispensing port system (134, FIG. 1) can be inserted and rest of the perimeter seal completed. In some examples, the two gaps 290 at the second end weld elements 284 of the two weld plates are sized and shaped to receive a dispensing port system to weld the dispensing port system to the flexible container at the same time the perimeter seal is formed. The first end or the opposite end of the dispensing port system can be left partially open or completely open, such as un-sealed, for purposes of filling the contents of the flexible container. The un-sealed end can subsequently be sealed after filling the contents of the flexible container. In an example, the sealed end opposite the dispensing port system can be provided with an enlarged perimeter seal and can include a perimeter defining a hole for hanging the flexible container. When a particular heat die incorporates a gap along the perimeter weld element 274, the gap allows an edge of a container formed thereby to be further manipulated, such as to be filled with a fluid. The open edge can subsequently be closed using another or a different set of heat dies.

A plurality of equally spaced or randomly spaced purging orifices 294 may be provided within the boundary defined by the perimeter weld element 174. The spaced purging orifices 294 allow trapped air to be purged or discharged during the heat welding procedure. In some examples, equally spaced or randomly spaced purging orifices 296 can also be provided through the central weld body section 270 outside of the boundary defined by the perimeter weld element 174 to similarly allow trapped air to be purged.

Figure 9B:
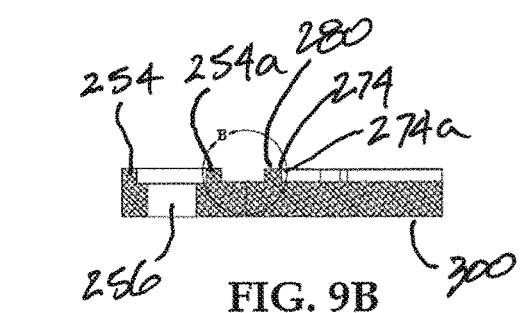
FIGS. 9B-9E are exploded views of different sections or parts of the heat die of FIG. 9A.

With reference now to FIG. 9B, a cross-sectional end view taken along line A-A of FIG. 9A is shown. As shown in the detailed view of FIG. 9B, the height or thickness of the perimeter rail 256 measured from the inside surface 254a to the exterior weld plate surface 300 is greater than the height or thickness measured from the weld surface 274a of the perimeter weld element 274 to the exterior weld plate surface 300. The height difference or offset defines the film welding space or gap 226 previously discussed with reference to FIGS. 6A-6E, and particularly with reference FIG. 6A. Said differently, when two weld plates are stacked, the two plates contact one another at the respective inside surfaces 254a of the perimeter rails 156. The offset gap at the two weld surfaces 274a, 274a of the two perimeter weld elements 274, 274 define the film welding space for welding the permanent seal section 202 and the pressure absorbing seal section 204 of the perimeter seal 200.

Figure 9C:
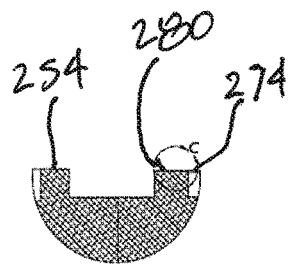

FIG. 9C is an enlarged view of detail B of FIG. 9B.

Figure 9D:
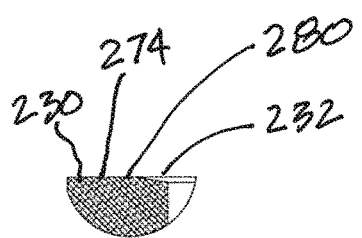
Figure 9E:
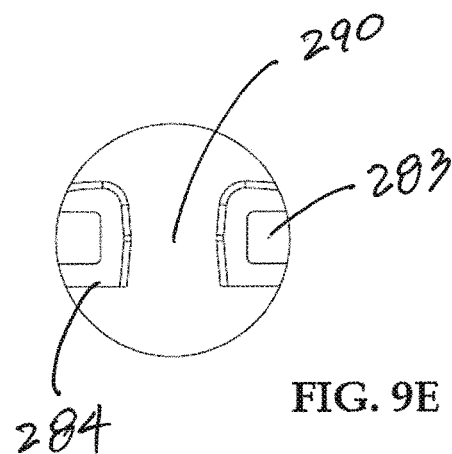

FIG. 9D is detail C of FIG. 9C. As shown, the side weld 280 of the perimeter weld element 274 has a permanent seal welding section 230 and a tapered pressure absorbing seal welding section 232. In the present example, the pressure absorbing seal welding section 232 is a simple tapered or inclined surface, which can resemble the pressure absorbing seal welding section 232 of FIG. 6C, discussed above. However, the pressure absorbing seal welding section 232 is not limited and can embody any of the pressure absorbing seal welding sections 232 described elsewhere herein.

FIG. 9B is an enlarged view of detail D of FIG. 9A.

Figure 10:
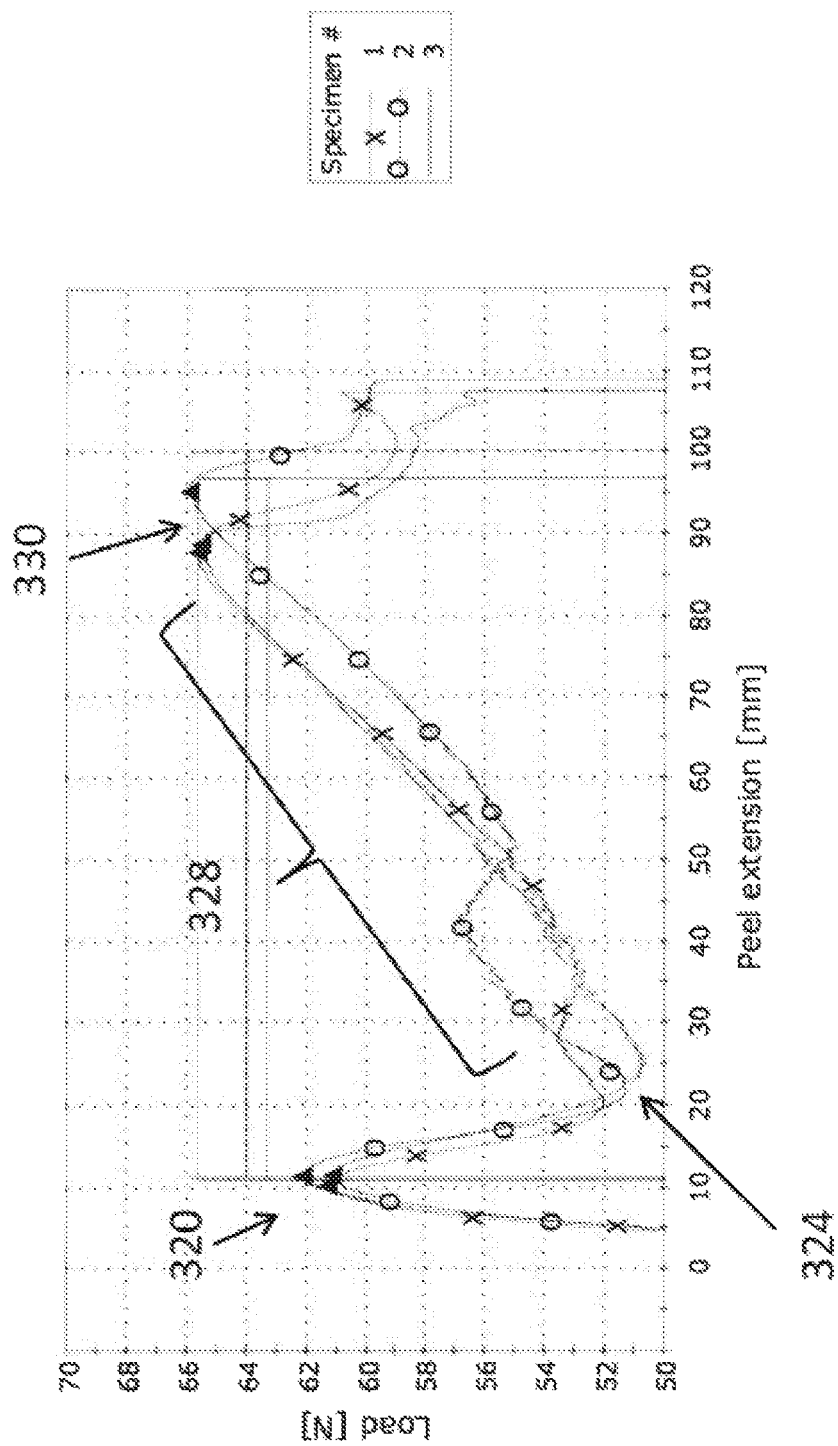
FIG. 10 shows a load to peel extension graph of three different flexible containers having the disclosed perimeter seal and their response characteristics when subjected to a load.

With reference now to FIG. 10, Load to Peel extension graphs showing tests of three samples from three different flexible containers each with a perimeter seal 200 provided in accordance with aspects of the present invention are shown. The Load along the Y-axis of the graph is shown as a measurement of force, measured in Newton. The Peel extension along the X-axis is shown as a measurement of distance, in this case in millimeters of deflection, which can be due to peeling or stretching of the pressure absorbing seal 204, the permanent seal 202, the front sheet, the rear sheet, or combinations thereof due to the load applied to the front and rear sheets, as further discussed below.

In arriving at the graphs, three flexible containers were formed using PP-based films similar to the PP-based films used in commercially available EXCEL® IV containers. In the present embodiment, the containers were formed using a film of about 0.2 mm thickness and provided with perimeter seals using the weld plate of FIG. 9A. The flexible containers were then filled with a liquid, sterilized, then stored for at least 48 hours before further testing. Subsequently, the three flexible container samples were drained and each container cut-up to form three separate test strips or test samples, each resembling that of FIG. 5 along an end section and about one inch in width and about four inches in length. Each test sample was then placed in a test apparatus and separately subjected to a pull test.

Using the test apparatus and with reference to FIG. 5, the front sheet 102 and the rear sheet 104 were separately secured to a respective clamp and then the two clamps were pulled apart under incrementally controlled loads. As shown in FIG. 10, for each test sample, the initial applied load quickly increases to a distinct peak at approximately region 320 with very little movement in the peel extension. Almost uniformly, all three samples produced a load value of between 61 Newton to 62.5 Newton at a peak region 320 and then rapidly drop in value. This rapid rise and then drop is a reflection of the pressure absorbing seal section 204 of the test strip rising to a load value that exceeds the seal value of the pressure absorbing seal section 204, which then causes the pressure absorbing seal section 204 to peel along the separation line 210 until the separation reaches the second transition 192b adjacent the permanent seal section 202. This is indicated on the graphs at approximately the drop region 324.

When each test strip is subjected to a continued load after the pressure absorbing seal section 204 separates, the relatively stronger strength of the permanent seal section 202 keeps the front and rear sheets together while the front and rear sheets that are not held together by the permanent seal section 202 begin to stretch under the continued load. This can be seen along the rising slope section of the graphs, along region 328 of the graphs.

Between drop region 324 and rising slope region 328, the data produced by the three test strips react differently. Without confining to any particular theory or position, it is believed that variation in results can be due to variation in film samples and different bonds at the permanent seal sections 202 of the three test strips. These differences appeared to lead to different performance reactions as indicated by the variance at the rising slope region 328.

When each test strip is subjected to a continued load after the pressure absorbing seal section 204 separates, the test strip rises to a second peak region 330, which is around 65-66 Newton. The second peak region 330, on average, has a higher load value than the load value of the first peak region 320. As shown and when the graphs are smoothed out, each graph describes an increasing slope, followed by a peak, followed by a decreasing slope, followed by an increasing slope, followed by a second peak, which is higher than the first peak, and then followed by a final decreasing slope.

Almost uniformly, all three test strips fail at the second peak region 330, or shortly thereafter. The second peak region 330 is indicative of the fail point of the test sample, which can be considered the point when the permanent seal section 202 fails by peeling or separating or the failure of at least one of the front and rear sheets, which can rupture or split.

The test strips and the results from testing the test strips as depicted by the graphs shown in FIG. 10 confirm that perimeter seals formed using heat dies and methods of the present invention will have a load to peel extension characteristic from a starting point, then an increasing slope, followed by a peak, followed by a decreasing slope, followed by an increasing slope, followed by a second peak, which is higher than the first peak, and then followed by a final decreasing slope. The first peak followed by a decreasing slope on the load to peel extension graph demonstrate that the perimeter seal 200 having both a pressure absorbing seal section 204 and a permanent seal section 202 will not peel or fail at the permanent seal section 202 until after the pressure absorbing seal section 204 of the permanent seal separates or fails. In particular examples, the permanent seal section 202 of the perimeter seal 200 will not peel or fail at least until after the load on the permanent seal section 202 increases. If the permanent seal section does separate or fail, the load value of the permanent seal will follow by a decrease in value.

Methods of making and using flexible containers and components thereof, including weld dies for use to make and use flexible containers, are within the scope of the present invention.

Although the preferred embodiments of flexible containers provided in accordance with aspects of the present devices, systems, and methods have been described with some specificity, the description and drawings set forth herein are not intended to be delimiting, and persons of ordinary skill in the art will understand that various modifications may be made to the embodiments discussed herein without departing from the scope of the disclosure, and all such changes and modifications are intended to be encompassed within the appended claims. Various changes to the container comprising different perimeter seals each with a permanent seal section and a pressure absorbing seal section are contemplated. For example, a same container may have a perimeter formed by more than one different heat die tooling described herein to form a perimeter with a perimeter seal having different seal characteristics along different length sections of the perimeter. Accordingly, many alterations and modifications may be made by those comprising ordinary skill in the art without deviating from the spirit and scope of the device, system, and method.

What is claimed is:

1. A flexible container comprising:
   a first sheet attached to a second sheet along a perimeter with a perimeter seal to define an enclosed space, said perimeter comprising first and second long edges and first and second short edges, and each of said first and second sheets comprises an exterior surface and an interior surface;
   wherein the perimeter seal has both a permanent seal section and a pressure absorbing seal section along a cross-section and is formed along at least one section of the first long edge and the second long edge and at least one section of the first short edge and the second short edge;
   wherein the pressure absorbing seal section of the perimeter seal has a separation characteristic value that is lower than the separation characteristic value of the permanent seal section;
   wherein the permanent seal section and the pressure absorbing seal section along the cross-section is asymmetric along a plane defined by the first sheet and the second sheet;
   wherein the pressure absorbing seal section of the at least one section of the first long edge and the second long edge and the pressure absorbing seal section of the at least one section of the first short edge and the second short edge are spaced from one another so as to define a space therebetween; and
   wherein the perimeter seal has a first peelable transition located adjacent the enclosed space formed by an edge of a heat die and a second peelable transition located between the permanent seal section and the pressure absorbing seal section away from the enclosed space formed by a transition section of the heat die away from the edge of the heat die.

2. The flexible container of claim 1, further comprising a peelable seal attaching the interior surfaces of the first and second sheets together and the peelable seal extending between the two long edges and connecting to the perimeter seal of the first and second long edges.

3. The flexible container of claim 1, wherein the permanent seal section and the pressure absorbing seal section extend an entire length of at least one of the first long edge, the second long edge, the first short edge, and the second short edge.

4. The flexible container of claim 1, further comprising a fluid dispensing system attached at the first short edge.

5. The flexible container of claim 4, wherein the fluid dispensing system comprises at least one nozzle.

6. The flexible container of claim 1, wherein the first sheet, the second sheet or both the first sheet and the second sheet are made from a polypropylene (PP) based material.

7. The flexible container of claim 1, wherein the permanent seal section has a width and the pressure absorbing seal section has a width, and wherein the width of the permanent seal section is at least two times greater than the width of the pressure absorbing seal section.

8. The flexible container of claim 1, further comprising an opaque protective cover located over the exterior surface of the front sheet.

9. The flexible container of claim 1, wherein the asymmetric permanent seal section and the pressure absorbing seal section along the cross-section is formed by a heat die set comprising a first heat die having a transition section located between a permanent seal welding section and a surface and a pressure absorbing seal welding section and a second heat die having a single generally planar or flat weld section.

10. The flexible container of claim 1, wherein the perimeter seal with the permanent seal section and the pressure absorbing seal section is formed along the entire first long edge and the entire second long edge.

11. A flexible container comprising:
    a first sheet attached to a second sheet along a perimeter with a perimeter seal to define an enclosed space, said perimeter comprising first and second long edges and first and second short edges, and each of said first and second sheets comprising an exterior surface and an interior surface;
    wherein the perimeter seal has both a permanent seal section and a pressure absorbing seal section along a cross-section and wherein the pressure absorbing seal section of the perimeter seal has a separation characteristic value that is lower than the separation characteristic value of the permanent seal section;
    wherein the cross-section of the perimeter seal with the permanent seal section and the pressure absorbing seal section comprises a separation line formed between the first sheet and the second sheet at the pressure absorbing seal section, and wherein the first sheet at the separation line has a variable thickness and a transition section and wherein the second sheet at the separation line has a generally constant thickness formed by a heat die with a generally flat surface;
    wherein the perimeter seal with the permanent seal section and the pressure absorbing seal section is located along at least a length of the first long edge;
    wherein the perimeter seal comprises an outer edge defined by the permanent seal section and an inner edge defined by the pressure absorbing seal section;
    wherein the outer edge and the inner edge are generally parallel to one another and the inner edge define at least part of the enclosed space; and
    wherein the perimeter seal has a first peelable transition located adjacent the enclosed space formed by an edge of a heat die and a second peelable transition located between the permanent seal section and the pressure absorbing seal section away from the enclosed space formed by a transition section of the heat die away from the edge of the heat die.

12. The flexible container of claim 11, wherein the permanent seal section and the pressure absorbing seal section along the cross-section is formed by a heat die set comprising a first heat die having a transition section located between a permanent seal welding section and a surface and a pressure absorbing seal welding section and a second heat die having a single generally planar or flat weld section.

13. The flexible container of claim 11, further comprising at least one peelable seal attaching the interior surfaces of the first and second sheets together and the at least one peelable seal extending between the two long edges.

14. The flexible container of claim 11, wherein the permanent seal section and the pressure absorbing seal section extend an entire length of the first long edge.

15. The flexible container of claim 11, further comprising a fluid dispensing system attached at the first short edge.

16. The flexible container of claim 15, wherein the fluid dispensing system comprises at least one nozzle.

17. The flexible container of claim 11, wherein the first sheet, the second sheet or both the first sheet and the second sheet are made from a polypropylene (PP) based material.

18. The flexible container of claim 11, wherein the permanent seal section has a width and the pressure absorbing seal section has a width, and wherein the width of the permanent seal section is at least two times greater than the width of the pressure absorbing seal section.

19. The flexible container of claim 11, further comprising an opaque protective cover located over the exterior surface of the front sheet.

20. A flexible container comprising:
a first sheet attached to a second sheet along a perimeter with a perimeter seal to define an enclosed space, said perimeter comprising first and second long edges and first and second short edges, and each of said first and second sheets comprises an exterior surface and an interior surface and an interior cavity defined by the first and second sheets;

wherein the perimeter seal has both a permanent seal section and a pressure absorbing seal section along a cross-section;

wherein the permanent seal has an outer edge only and the pressure absorbing seal has an inner edge only and the inner and outer edges are generally parallel to one another;

wherein the inner edge of the first long edge is spaced from the inner edge of the second long edge;

wherein the pressure absorbing seal section of the perimeter seal has a separation characteristic value that is lower than the separation characteristic value of the permanent seal section;

wherein the permanent seal section and the pressure absorbing seal section along the cross-section is asymmetric along a plane defined by the first sheet and the second sheet; and wherein the perimeter seal has a first peelable transition located adjacent the enclosed space formed by an edge of a heat die and a second peelable transition located between the permanent seal section and the pressure absorbing seal section away from the enclosed space formed by a transition section of the heat die away from the edge of the heat die.

21. The flexible container of claim 20, further comprising a fluid dispensing system attached at the first short edge.

22. The flexible container of claim 21, wherein the fluid dispensing system comprises at least one nozzle.

23. The flexible container of claim 20, further comprising a peelable seal located between the first short edge and the second short edge and in contact with the pressure absorbing seal section of the first long edge and the second long edge.

* * * * *